United States Patent [19]

Connor et al.

[11] Patent Number: 4,764,525

[45] Date of Patent: Aug. 16, 1988

[54] N-1H-TETRAZOL-5-YLBENZAMIDES HAVING USE AS ANTIALLERGY AND ANTIINFLAMMATORY AGENTS

[75] Inventors: David T. Connor, Ann Arbor; Michael D. Mullican, Ypsilanti, both of Mich.

[73] Assignee: Warner-Lambert Company, Morris Plains, N.J.

[21] Appl. No.: 18,680

[22] Filed: Feb. 25, 1987

[51] Int. Cl.$^4$ ................. A61K 31/41; C07D 257/04
[52] U.S. Cl. ................................. 514/381; 548/251
[58] Field of Search ..................... 548/251; 514/381

[56] References Cited

U.S. PATENT DOCUMENTS 4,146,631  3/1979  Ford et al. ................... 548/253
4,474,792 10/1984  Erickson ...................... 548/253

FOREIGN PATENT DOCUMENTS 2006782 10/1978  United Kingdom .

Primary Examiner—Glennon H. Hollrah
Assistant Examiner—D. B. Springer
Attorney, Agent, or Firm—Joan Thierstein

[57] ABSTRACT

The present invention is novel 2-isopropoxy-N-1H-tetrazol-5-yl-benzamides having unexpected inhibition of histamine release from human basophils.

8 Claims, No Drawings

N-1H-TETRAZOL-5-YLBENZAMIDES HAVING USE AS ANTIALLERGY AND ANTIINFLAMMATORY AGENTS

BACKGROUND OF THE INVENTION

Various N-1H-tetrazol-5-yl carboxamides have been disclosed as antiallergy agents. Particularly, selected N-(tetrazol-5-yl)benzamides having antiallergic activity are disclosed. For example, U.S. Pat. No. 4,146,631 and British Patent Application No. 2,006,782 disclose various hydroxy substituted N-(tetrazol-5-yl)benzamides and U.S. Pat. No. 4,474,792 discloses methoxy, ethoxy and methylthio substituted N-(tetrazol-5-yl)benzamides having antiallergic activity.

However, novel compounds of the present invention are now found to provide advantageous activity not within that expected by one of skill in the art even in view of the above noted references. The activity is demonstrated by inhibition of histamine release from human basophils in an assay hereinafter referred to as the HHB assay.

Thus, the present invention is for compounds of the formula I as defined hereinafter as well as pharmaceutical compositions for use as antiallergy agents containing the compounds of formula I and to methods of treating allergy in mammals, particularly humans, suffering therefrom, by administering compounds of formula I to the mammals in unit dosage form.

SUMMARY OF THE INVENTIONS

The present invention is a novel compound of the formula (I)

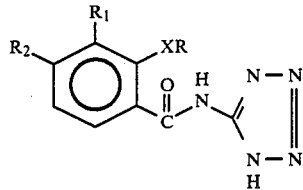

or pharmaceutically acceptable salts thereof; wherein X is oxygen or sulfur; R is isopropyl, $R_1$ is hydrogen, chloro, fluoro, bromo, or iodo; and $R_2$ is alkoxy.

DETAILED DESCRIPTION OF THE INVENTION

The tetrazole ring in the compounds of the invention exists in tautomeric form such that the hydrogen is on either the $N^1$ or $N^2$ atoms of the ring, i.e.,

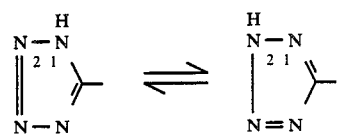

However, for convenience, hydrogen is depicted herein simply as appearing on the $N^1$ atom.

In general the procedure for preparing the novel compounds of the present invention is as shown in the following Scheme 1.

SCHEME 1

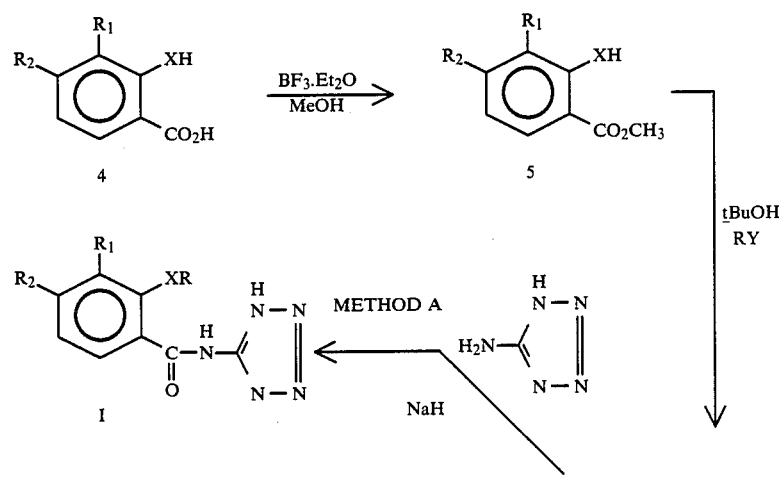

SCHEME 1

-continued

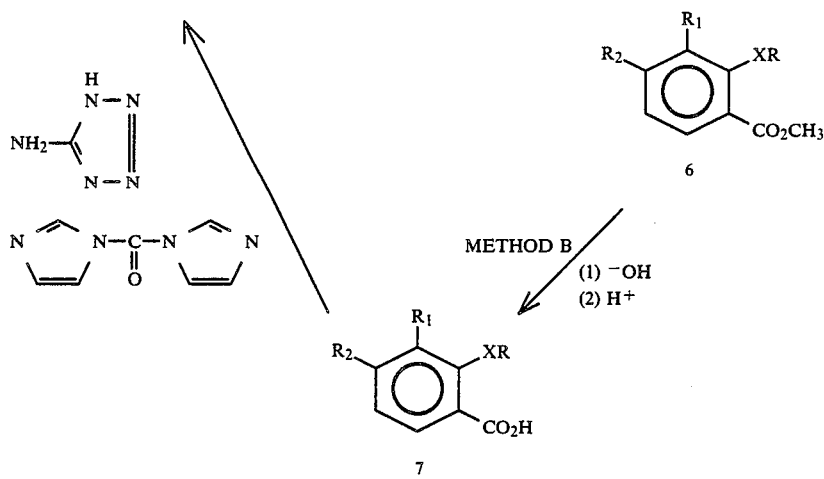

Generally, benzoic acid derivatives of formula 4 wherein X, $R_1$, and $R_2$ are as defined above are esterified to yield salicylate of formula 5 wherein X, $R_1$, and $R_2$ are as defined above and the XH group of the salicylates of the formula 5 are alkylated to provide the isopropoxy or isopropylthio derivatives of formula 6 wherein X, R, $R_1$, and $R_2$ are as defined above. Reagents of the formula RY include isopropyl halides, and isopropyl sulfonates and isoureas. Alkylation conditions are analogous to those described by Mathias, C. J., *Synthesis*, 1979, p. 561.

The isopropoxy or isopropylthio derivatives of the formula 6 are saponified to yield an acid of formula 7 wherein X, R, $R_1$, and $R_2$ are as defined above as shown by Method B in Scheme 1 above. The acids of the formula 7 are then converted to the compounds of the formula I by coupling with 5-aminotetrazole. Coupling reagents may include 1,1'-carbonyldiimidazole, 1,3-dicyclohexylcarbodiimide (DCC), or other peptide coupling agents.

Alternatively the esters of the formula 6 may be converted directly to the compounds of formula I as shown in Method A of Scheme 1 by treating a slurry of an oil dispersion of sodium, lithium, or potassium hydride in dimethyl sulfoxide with 5-aminotetrazole. A solution of the esters of the formula 6 also in dimethyl sulfoxide is added dropwise to the resulting slurry to obtain the compounds of the formula I. The procedure of Method A is analogous to that described by Singh, B., in *Tetrahedron Lett.*, 1971, p. 321.

The salicylic acids of the formula 4 wherein $R_1$, $R_2$, and $R_3$ as defined above, are commercially available or are prepared in the following Scheme 2 from the corresponding phenoxide of the formula 8a wherein X, $R_1$, and $R_2$ are as defined above and Q is $Na^+$ or $K^+$ by a Kolbe-Schmitt reaction or by the Marasse modification of the Kolbe-Schmitt reaction using the corresponding phenol 8b wherein Q is $H^+$ in the presence of sodium or potassium carbonate.

SCHEME 2

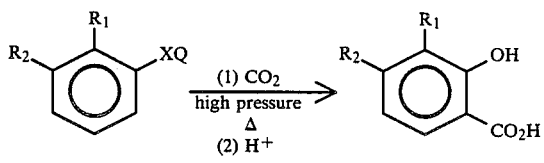

8a Q = $Na^+$, $K^+$
8b Q = $H^+$ (For examples of both procedures see: Baine, O.; Adamson, G. F.; Barton, J. L.; Fitch, J. L.; Swayampati, D. R.; Jeskey, H. *J. Org. Chem.*, 1954, 19, 510.)

More specifically, Scheme 3 shows compound of the formula 9 is prepared by adding a mixture methyl 4-methoxy-2-(l-methylethoxy)benzoate of the formula (10) and chlorotrimethylsilane to a $-70°$ C. $-78°$ C. tetrahydrofuran solution of lithium diisopropylamide to give methyl 4-methoxy-2-(1-methylethoxy)-3-(trimethylsilyl)benzoate (11) regioselectively.

Compound of the formula 11 is converted to the formula 9 by treatment with N-bromosuccinimide (NBS) or bromine in methylene chloride. (For examples, see: Hafner, K.; Lehn, J. M.; Rees, C. W.; Schleyer, P. V. R.; Trost, B. M.: Zahradnik, R., Ed., "Silicon Reagents for Organic Synthesis," Springer-Verlag: New York, 1983; Chapter 8).

SCHEME 3

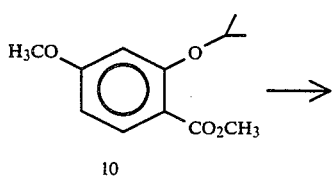

-continued
SCHEME 3

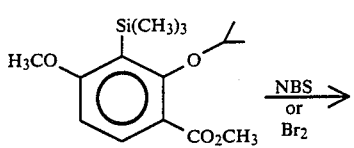

11

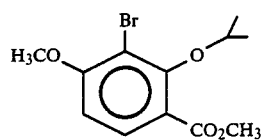

9

Further, Scheme 4 shows a compound of the formula 12 is prepared from a compound of the formula 13 using iodine monobromide or iodine or iodine monochloride in methylene chloride (for examples, see: Félix, G.; Dunoguès, J.; Pisciotti, F.; Calas, R., *Angew. Chem. Int. Ed. Engl.*, 1977, 16, 488).

SCHEME 4

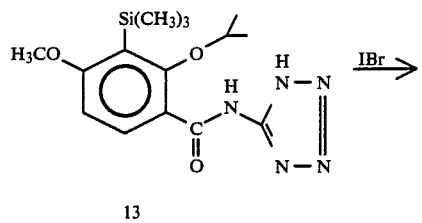

13

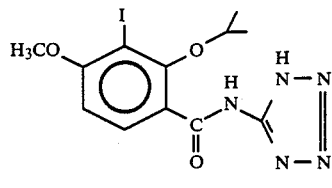

12

A compound of the formula 14 is prepared from 4-bromosalicylic acid of formula 15 by a method analogous to that described for the preparation of 2-bromophenol (see: Huston, R. C.; Ballard, M. M., "Organic Synthesis," John Wiley and Sons: New York, 1943; Collect. Vol. II, p. 97) and shown as follows in Scheme 5.

SCHEME 5

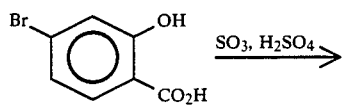

15

-continued
SCHEME 5

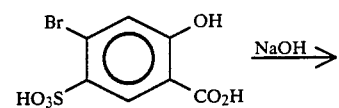

16

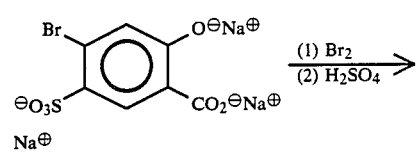

17

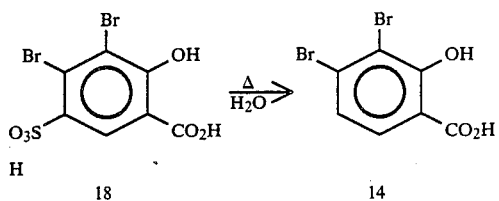

18     14

Particularly, 4-bromosalicylic acid of the formula 15 is treated with fuming sulfuric acid to give a sulfonic acid of formula 16. Treatment of the acid of the formula 16 with sodium hydroxide gives the sodium salt of formula 17 which is brominated with bromine followed by acidification to give a compound of formula 18. Steam distillation afforded 3,4-dibromosalicylic acid of the formula 14. Intermediates of the formulae 16–18 are not isolated or characterized.

The starting materials required for the processes described in this invention are either commercially available or can be synthesized by methods known in the art.

The compounds of formula I are useful both in the free acid form, in the form of base salts, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfamate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compound of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine amino acids such as arginine, and lysine; guanidine; N-methylglucosamine; N-methylpiperazine; morpholine ethylenediamine; N-benzylphenethylamine tris(hydroxymethyl)aminomethane; and the like. (See for example, "Pharmaceutical Salts," *J. Pharm. Sci.*, 66(1), 1–19 (1977).)

The salts are prepared by reacting the compound I having an acid group thereon with a base such that the reactions are in an organic solvent, in which case the salt separates directly or can be obtained by concentration of the solution.

The base salts of compounds of formula I described above are prepared by reacting the appropriate base with a stoichometric equivalent of the acid compounds of formula I to obtain pharmacologically acceptable base salts thereof.

The compounds of this invention may also exist in hydrated or solvated forms.

The products of the reactions described herein are isolated by conventional means such as extraction, distillation, chromatography and the like.

The antiallergic activity not within that expected of the compounds having the formula I of the present invention is shown by an assay determining inhibition of the release of histamine from human basophils (HHB). A description of the protocol for the HHB assay is found hereinafter.

Thus, pharmaceutical compositions are prepared from the compounds of formula I and salts thereof described as the present invention in unit dosage form comprising the compound either alone or in admixture with a pharmaceutically acceptable carrier appropriately selected from those known.

A physician or veterinarian of ordinary skill readily determines a subject who is exhibiting allergic or inflammatory symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies. They may also be introduced parenterally (e.g., subcutaneously, intravenously, or intraintramuscularly), using forms known to the pharmaceutical art. They are also introduced directly to an affected area, (e.g., in the form of eye drops or by inhalation). For the treatment of allergic or inflammatory conditions such as erythema, the compounds of the present invention may also be administered topically in the form of ointments, creams, gels, or the like. In general, the preferred route of administration is orally.

An effective but nontoxic quantity of the compound I is employed in treatment. The ordinarily skilled physician or veterinarian will readily determine and prescribe the effective amount of the antiallergic or antiinflammatory agent to prevent or arrest the progress of the condition. The dosage regimen is selected in accordance with a variety of factors including the type, age, weight, sex, and medical condition of the mammal, the severity of symptoms of the disease being treated, the route of administration and particular compound of formula I employed. An ordinarily skilled physician or veterinarian will readily determine and prescribe the effective amount of the compound I to prevent or arrest the progress of the condition. In so proceeding, the physician or veterinarian could employ relatively low dosages at first, subsequently increasing the dose until a maximum response is obtained. For convenience, the total daily dosage may be divided and administered in portions during the day if desired. In so proceeding the physician or veterinarian could employ relatively low dosages at first, subsequently increasing the dose until a maximum response is obtained.

Initial dosages of the compounds of the invention having formula I are ordinarily in the area of 10 mg up to 2 g per day orally, preferably 10 mg to 500 mg per dose orally, given from one to four times daily or as needed. When other forms of administration are employed equivalent doses are administered.

It is understood that the compositions and methods of treatment of the present invention as described above also include the free acid, and the pharmacologically acceptable base salts of the compounds of formula I.

The following examples further illustrate the invention, but are not meant to be limiting thereto.

EXAMPLE 1

4-Methoxy-2-(1-methylethoxy)-N-1H-tetrazol-5-ylbenzamide

Step 1

A solution of 10.0 g (54.9 mmol) methyl 4-methoxysalicylate in 35 ml of dimethyl sulfoxide is treated dropwise with 7.4 g (65.9 mmol) of potassium t-butoxide in 75 ml of dimethylsulfoxide. The resulting pale yellow solution is stirred at 25° C. under nitrogen for 70 minutes. Then 19.7 g (159.8 mmol) of 2-bromopropane is added and the resulting mixture is stirred at 25° C. for 70 hours. The reaction mixture is poured onto 400 ml of $H_2O$ and the resulting solution is extracted with diethyl ether (3×125 ml). The combined extracts are washed with aqueous saturated NaCl, dried ($Na_2SO_4$) and concentrated in vacuo to give 8.5 g of the crude product as a yellow oil. Flash chromatography ($SiO_2$, 18×65 cm, 15% ethyl acetate-hexane) gives 7.45 g (12.31 g theoretical, 61%) of analytically pure methyl 4-methoxy-2-(1-methylethoxy)benzoate as a colorless oil.

Step 2

A solution of 3.0 g (35.3 mmol) of anhydrous 5-aminotetrazole in 20 ml of dimethyl sulfoxide is added dropwise to a 15° to 20° C. slurry of 2.8 g (70.0 mmol) of 60% NaH (oil dispersion) in 75 ml of dimethyl sulfoxide under nitrogen atmosphere. The resulting mixture is stirred at 25° C. for 2.5 hours. A solution of 6.50 g (28.98 mmol) of methyl 4-methoxy-2-(1-methylethoxy)benzoate in 25 ml of dimethyl sulfoxide is added dropwise to the reaction and stirred at 25° C. for 18 hours. The reaction is poured onto 600 g of ice-water and the resulting aqueous solution is acidified with aqueous 10% HCl. The product is isolated by vacuum filtration and recrystallization from 95% ethanol gives 1.90 g (8.03 g theoretical, 24%) of the analytically pure 4-methoxy-2-(1-methylethoxy)-N-1H-tetrazol-5-ylbenzamide as fine, white needles having a melting point of 212° –213° C.

EXAMPLE 2

3-Bromo-4-methoxy-2-(1-methylethoxy)-N-1H-tetrazol-5-ylbenzamide.

Step 1

A solution of 15.80 ml (24.49 mmol) of 1.55M n-BuLi(butyl lithium)/hexane is added to a −70° C. solution of 2.48 g (24.54 mmol) of diisopropylamine in 60 ml of tetrahydrofuran under nitrogen atmosphere. The reaction is warmed to 0° C. and stirred for 15 minutes, then recooled to −70° C. The freshly generated lithium diisopropylamide is treated with a solution of 5.00 g (22.30 mmol) of methyl 4-methoxy-2-(1-methylethoxy)benzoate (prepared by the method of Step 1 of Example 1) and 4.79 g (44.12 mmol) of chlorotrimethylsilane in 15 ml of tetrahydrofuran. The reaction is stirred for five hours as the bath slowly warms to 12° C. The bath is removed and the reaction is stirred at room temperature for 15 hours. The reaction is poured onto 400 ml of aqueous saturated NH4Cl and extracted with diethyl ether (3×100 ml). The combined extracts are washed with aqueous saturated NaCl, dried (Na2SO4) and concentrated in vacuo. Flash chromatography (SiO2, 6.5×27 cm, 10% ethyl acetate-hexane) gives 3.98 g (6.61 g theor., 60%) of methyl 4-methoxy-2-(1-methylethoxy)-3-(trimethylsilyl)benzoate as a colorless oil.

Step 2

A solution of 2.85 g (9.61 mmol) of methyl 4-methoxy-2-(1-methylethoxy)-3-(trimethylsilyl) benzoate (prepared by the method of Step 1) in 10 ml of CH2Cl2 is added dropwise to a 0° C. slurry of 3.05 g (17.14 mmol) of N-bromosuccinimide (NBS) in 30 ml of CH2Cl2 under nitrogen. The reaction is stirred for 31.5 hours while slowly warming to room temperature. The reaction is concentrated in vacuo, the residue is suspended in diethyl ether and filtered and the filtrate is concentrated in vacuo. The residue is resuspended in diethyl ether/hexane (1:1), filtered, and the filtrate concentrated in vacuo to give an oil. Flash chromatography (SiO2, 20% ethyl acetate-hexane, 6.5×26 cm) afforded 2.52 g (2.91 g theor., 87%) of analytically pure methyl 3-bromo-4-methoxy-2-(1-methylethoxy)benzoate as a colorless oil.

Step 3

The oil, methyl 3-bromo-4-methoxy-2-(1-methylethoxy)benzoate, (2.34 g, 7.72 mmol) prepared in Step 2 above is dissolved in 26 ml of a methanol-water-tetrahydrofuran (9:16:1) mixture and treated with 11.5 ml (11.50 mmol) of aqueous 1N NaOH. The reaction is stirred at 25° C. for 65 hours, poured onto 200 ml of cold H2O, then acidified with aqueous 10% HCl. The aqueous mixture is extracted with ethyl acetate (3×). The combined extracts are washed with an aqueous staturated NaCl solution, dried (Na2SO4) and concentrated in vacuo to give 23 g of a white solid. Recrystallization from ethyl acetate-hexane gives 1.66 g (2.32 g theoretical, 74%) of analytically pure 3-bromo-4-methoxy-2-(1-methylethoxy)benzoic acid as white needles having a melting point of 109°–110° C.

Step 4

A mixture of 1.28 g (4.43 mmol) 3-bromo-4-methoxy-2-(1-methylethoxy)benzoic acid (prepared in Step 3) and 0.83 g 5.12 g (5.12 mmol) of 1,1′-carbonyldiimidazole in 15 ml of acetonitrile is warmed at reflux under nitrogen atmosphere (or CaCl2 filled drying tube) for one hour. The reaction mixture is treated with 1.07 g (10.62 mmol) of triethylamine and 0.44 g (5.17 mmol) of anhydrous 5-aminotetrazole. The resulting mixture is warmed at reflux for 30 hours. The reaction mixture is then poured onto 180 g of ice water and acidified with aqueous 10% HCl and filtered to give 1.32 g (1.58 theor., 84%) of 3-bromo-4-methoxy-2- 1-methylethoxy)-N-1H-tetrazol-5-ylbenzamide as a white solid having melting point 255°–256° C.

EXAMPLE 3

5-Bromo-4-methoxy-2-(1-methylethoxy)-N-1H-tetrazol-5-ylbenzamide

Step 1

A solution of 9.0 g (56.5 mmol) of bromine in 5 ml of CH2Cl2 is added dropwise to a 0° C. solution of 10.0 g (54.9 mmol) of methyl 4-methoxysalicylate in 90 ml of CH2Cl2. The reaction is stirred at 0° C. to 25° C. over five hours and then concentrated in vacuo to give 13.9 g of methyl 5-bromo-4-methoxysalicylate as a white solid: mp 141°–143° C.) (lit mp 143°–144° C.), Cresp, T. M.; Sargent, M. V.; Elix, J. A.; Murphy, D. P. H., *J. Chem. Soc., Perkin Trans.*, 1, 1973, 340). The material is sufficiently pure to be used in the subsequent reaction.

Steps 2 and 3

Using the method of Step 1 of Example 1 and 3 of Example 2 above, the above salicylate (12.0 g, 50.0 mmol) is converted to 3.69 g (14.46 g theor., 25%) of analytically pure 5-bromo-4-methoxy-2-(1-methylethoxy)benzoic acid, as a white, crystalline solid: mp 122°–124° C. (t-butyl methyl ether).

Step 4

Using the method of Step 4 of Example 2, the above carboxylic acid (3.01 g, 10.41 mmol) is converted to 3.20 g (3.71 g theor., 86%) of analytically pure 5-bromo-4-methoxy-2-(1-methylethoxy)-N-1H-tetrazol-5-ylbenzamide as a white solid: mp 265°–270° C. (dec).

EXAMPLE 4

3-Iodo-4-methoxy-2-(1-methylethoxy)-N-1H-tetrazol-5-ylbenzamide

A solution of 2.45 g (11.85 mmol) of iodine monobromide (IBr) in 12 ml of CH2Cl2 is added dropwise to a 0° C. solution of 4.00 g (11.45 mmol) of 4-methoxy-2-(1-methylethoxy)-N-1H-tetrazol-5-yl-3-(trimethylsilyl)-benzamide (prepared by a method analogous to Step 3 and 4 of Example 2 from methyl 4-methoxy-5-(trimethylsilyl)benzoate of Step 1 of Example 2 in 28 ml of CH2Cl2 under nitrogen atmosphere. The reaction is stirred for 15 minutes at 0° C. and one hour at room temperature. The reaction is concentrated in vacuo and the resulting solid was suspended in hexane and filtered, washing with diethyl ether. Recrystallization from dimethylformamide-water gives 3.29 g (4.62 g theor., 71%) of analytically pure carbamoyltetrazole as a white fluffy solid: mp 265°–270° C. (dec).

The usefulness of the compounds of the present invention as inhibitors of histamine release is demonstrated by the following tests particularly the assay for histamine release from human basophils or HHB. The HHB test is essentially as generally accepted among the ordinarily skilled artisans to show activity having unique usefulness to treat the diseases or conditions as set out in the present invention.

HISTAMINE RELEASE FROM HUMAN BASOPHILS (hereinafter HHB)

The HHB assay quantitates active histamine release and its inhibition by drugs, from basophils of human blood. Thus, the assay provides evaluation of the compounds of formula I for treating the conditions or diseases as is the present invention. As described herein the assay includes modifications of the method described by R. P. Siroganian in "An Automated Continuous-Flow System for the Extraction and Fluorometric Analysis of Histamine," *Anal. Biochem.*, 57, 383-394 (1974).

METHODS

Preparation of Leukocytes

Seventy ml of blood are drawn from allergic donors (chosen on the basis of adequate histamine induced by a challenge), using standard venipuncture methods, into 10 ml Vacutainers with 0.08 ml/tube 15% EDTA in water as anticoagulant. The blood samples are placed briefly on a rotary mixer. All glassware contacting the blood is siliconized. The blood is aliquoted into three plastic 50 ml centrifuge tubes and the volume is noted. Hespan (hydroxy ethyl starch), 0.5 ml per 1.0 ml of blood, is added. The tubes are inverted several times to mix and are left undisturbed at room temperature until a sharp separation is observed between the settled red cells and the leukocyte and platelet-rich plasma. This usually occurs within 35-45 minutes.

The plasma fraction is pipetted off and placed into two clean plastic 50 ml centrifuge tubes. The tubes are centrifuged for 12 minutes at 4° C. in a a 100 ml volumetric flask and 0.5 ml DMSO is added. If the compound does not dissolve readily, it is warmed gently on a hotplate and approximately 30 ml of distilled water is added. If the compound is in solution, distilled water is used to bring it up to 100 ml total volume. If the drug is not in solution, 0.2 ml 1N NaOH (or HCl) is added, and then distilled water is added to yield 100 ml total solution. Five ml of the stock solution is diluted (1:2) with 5 ml of two times concentrated HACM buffer to yield the stock working concentration of 150 $\mu$M. When added to the cells and stimulus, a final test concentration of 100 $\mu$M drug results (400 $\mu$l drug, 100 $\mu$cells and 100 $\mu$challenge agent or vehicle). Further dilutions are made with HACM buffer for 33, 10, 3.3, 1.0 $\mu$M, etc.

Challenge Agent Preparation

Short ragweed and house dust extracts (Greer Laboratories, Inc.) are supplied as aqueous extracts in stock concentrations of 40,000 and 10,000 protein nitrogen units per milliliter (PNU/ml), respectively. Aqueous solutions of anti-IgE antisera (rabbit-raised antibody) are purchased from Dako via Accurate Chemicals. The tripeptide f-met-leu-phe (fmlp) from Vega Biochemicals is used. The aqueous solutions of ragweed, house dust, and anti-IgE are diluted 1:2 with two times concentrated HACM and then further diluted with HACM to yield final stock concentrations of 6000 PNU/ml for ragweed and house dust, and a 1:50 dilution for the anti-IgE antisera. For fmlp, 28.5 mg of the tripeptide is dissolved in 1 ml of DMSO or 1 ml glacial acetic acid, then 49 ml distilled water and 50 ml of two times HACM are added to yield a final stock of 600 $\mu$M in HACM. The pH is adjusted to 7.4. Further dilutions for working solutions are made in HACM buffer. All stock and working solutions are stored at 4° C. Working solutions comprise 1/6 of the final volume in the cell reaction, therefore, working solutions of challenge agents are made up six times the required final concentration (i.e., 600 $\mu$M f-met-leu-phe yields 100 $\mu$M final concentration in the cellular reaction).

Protocol Design

Samples are run in triplicate, using either 1.5 ml polypropylene-capped reaction tubes, or 5.0 ml plasticuncapped tubes. Test compounds and challenge agents are prepared in HACM buffer, as described above. Fixed volume pipettes are used.

Test compound or vehicle control is added to three reaction tubes at 1.5× the final desired concentration (i.e., 400 $\mu$of test compound per 600 $\mu$total reaction volume). One hundred $\mu$of cells is added to each tube and the mixture is incubated for eight minutes at room temperature, and two minutes at 37° before antigen or other stimulus challenge. One hundred $\mu$of the challenge agent at 6× the final concentration is then added, and the final mixture is incubated at 37° C. for 45 minutes in a shaking water bath. This ensures that the cell preparation is constantly in suspension. The reaction is stopped by centrifugation at 2000 RPM for three minutes at 4° C. The supernate ($\approx$500 $\mu$) is poured into 2.0 ml antoanalyzer beakers and assayed for histamine by the fluorometric method.

In each experiment, cells from one donor are challenged with one or more of the challenge agents, according to the designed protocol and the previously determined sensitivity of the donor to particular challenge agents. Short ragweed and house dust concentrations are expressed in PNU/ml, fmlp challenges are in micromolar concentration ($\mu$M), and anti-IgE antisera and C5a challenges are in dilutions, e.g., IE-5 (1:100,000), 3E-5 (1:30,000), and 1E-4 (1:10,000).

Calculation and Interpretation of Results

The total histamine concentration in the "total" (acid-treated) samples must be 15 ng/ml to be acceptable. Spontaneous release of histamine from the cells should not exceed 15% of the total histamine, and is frequently <5%. The maximum percentage histamine released varies with the donor. The net amount released by the challenge agent must exceed 25% of the total cellular histamine to confidently assess inhibition by test compounds. Spontaneous histamine release is subtracted from both "totals" and challenged cells to calculate net percent release. Percent inhibition is calculated using the following formula:

$$1 - \left[ \frac{\text{Mean net \% release treated samples}}{\text{Mean net \% release for challenged control}} \right] \times$$

$$100 = \% \text{ inhibition}$$

Using the HHB assay the compounds of formula I are generally shown by the examples tested to inhibit the release of histamine from human basophils challenged with antigen and, thus, to have activity different from that expected by an ordinarily skiled artisan.

The results are shown in the table as follows:

TABLE

| | HHB TEST |
|---|---|
| Example No. | % Inhibition of Histamine Release with Anti-IgE Stimulus (tested at [33 $\mu$M]) |
| 1 | 41 |
| 2 | 60 |
| 3 | 28 |
| 4 | 73 |

Accordingly, the present invention also includes a pharmaceutical composition for treating one of the above diseases or conditions comprising an antidisease or anticondition effective amount of a compound of the formula I as defined above together with a pharmaceutically acceptable carrier.

The present invention further includes a method for treating one of the above named diseases or conditions in mammals, including man, suffering therefrom comprising administering to such mammals either orally or parenterally, preferably oral, a coresponding pharmaceutical composition containing a compound of formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents. It can also be encapsulating material. In powders, the carrier is a finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcelulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, aritificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid prepartions containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself or it can be the appropriate number of any of these in packaged form.

The quantity of active compound in a unit dose of preparation may be varied or adjusted from 10 mg to 2000 mg preferably to 10 mg to 500 mg according to the particular application and the potency of the active ingredient. The compositions can, if desired, also contain other compatible therapeutic agents.

We claim:

1. A compound of the formula (I)

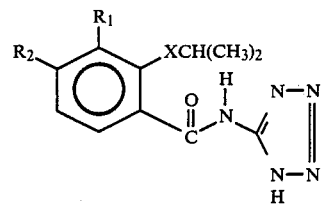

or pharmaceutically acceptable salts thereof; wherein
X is oxygen or sulfur;
$R_1$ is hydrogen, bromo, chloro, fluoro, or iodo and $R_2$ is alkoxy.

2. A compound of claim 1 wherein X is oxygen.

3. A compound of claim 2 wherein the embodiment is 4-methoxy-2-(isopropoxy)-N-1H-tetrazol-5-ylbenzamide.

4. A compound of claim 2 wherein the embodiment is 3-bromo-4-methoxy-2-(isopropoxy)-N-1H-tetrazol-5-ylbenzamide.

5. A compound of claim 2 wherein, the embodiment is 3-iodo-4-methoxy-2-(isopropoxy)-N-1H-tetrazol-5-ylbenzamide.

6. A compound which is 5-bromo-4-methoxy-2-(isopropoxy)-N-1H-tetrazol-5-ylbenzamide.

7. A pharmaceutical composition for treating diseases or conditions which benefit from inhibition of histamine release from basophils which comprises amount effective to inhibit histamine release of a compound of claim 1 and a pharmaceutically acceptable carrier.

8. A method of treating allergies in mammals which comprises administering to such mammal in need thereof an effective amount of a pharmaceutical compound according to claim 1.

* * * * *